(12) United States Patent
Guerfi et al.

(10) Patent No.: US 9,412,999 B2
(45) Date of Patent: Aug. 9, 2016

(54) POTATO-SHAPED GRAPHITE PARTICLES WITH LOW IMPURITY RATE AT THE SURFACE, METHOD FOR PREPARING THE SAME

(71) Applicant: HYDRO QUEBEC, Montreal, Quebec (CA)

(72) Inventors: Abdelbast Guerfi, Brossard (CA); Fernand Brochu, Longueuil (CA); Kimio Kinoshita, Cupertino, CA (US); Karim Zaghib, Longueuil (CA)

(73) Assignee: HYDRO-QUEBEC, Montreal, Quebec (CA)

( * ) Notice: Subject to any disclaimer, the term of this patent is extended or adjusted under 35 U.S.C. 154(b) by 0 days.

(21) Appl. No.: 14/878,742

(22) Filed: Oct. 8, 2015

(65) Prior Publication Data

US 2016/0141603 A1 May 19, 2016

Related U.S. Application Data

(63) Continuation of application No. 13/857,861, filed on Apr. 5, 2013, now Pat. No. 9,184,437, which is a continuation of application No. 12/572,510, filed on Oct. 2, 2009, which is a continuation of application (Continued)

(30) Foreign Application Priority Data

Oct. 25, 2000 (CA) ..................................... 2324431

(51) Int. Cl.
*C01B 31/04* (2006.01)
*H01M 4/133* (2010.01)
(Continued)

(52) U.S. Cl.
CPC ............ *H01M 4/133* (2013.01); *B01J 20/3204* (2013.01); *B01J 20/3236* (2013.01);
(Continued)

(58) Field of Classification Search
CPC ...................................................... C01B 31/04
USPC ......................................................... 423/448
See application file for complete search history.

(56) References Cited

U.S. PATENT DOCUMENTS

| 3,440,181 A | 4/1969 | Olstowski |
| 4,054,687 A | 10/1977 | Kunz |

(Continued)

FOREIGN PATENT DOCUMENTS

| EP | 0782207 A1 | 7/1997 |
| EP | 0916618 A1 | 5/1999 |

(Continued)

OTHER PUBLICATIONS

Jiang, W., et al., "Thermal Analysis of the Oxidation of Natural Graphite—Effect of Particles Size", Thermochimica Acta 351 (2000), pp. 85-93, Elsevier Science B.V., The Netherlands.

(Continued)

*Primary Examiner* — Daniel C McCracken
(74) *Attorney, Agent, or Firm* — Buchanan Ingersoll & Rooney P.C.

(57) ABSTRACT

Modified graphite particles obtained from graphite or based on graphite, the said particles having impurities in their internal structure and having on the surface a low, even nil, rate of an impurity or several impurities. In addition, these particles have at least one of the following characteristics:
  a tab density between 0.3 and 1.5 g/cc;
  a potatolike shape; and
  a granulometric dispersion such that the D90/D10 ratio varies between 2 and 5 and the particles have a size between 1 and 50 μm.
These particles can be used for fuel cells, electrochemical generators, or as moisture absorbers and/or oxygen absorbers and they have important electrochemical properties. The electrochemical cells and batteries thus obtained are stable and safe.

20 Claims, 12 Drawing Sheets

Related U.S. Application Data

No. 11/606,231, filed on Nov. 30, 2006, now abandoned, which is a continuation of application No. 10/381,843, filed as application No. PCT/CA01/01511 on Oct. 24, 2001, now abandoned.

(51) Int. Cl.

| | | |
|---|---|---|
| B01J 20/32 | (2006.01) | |
| H01M 4/1393 | (2010.01) | |
| H01M 4/583 | (2010.01) | |
| H01M 4/96 | (2006.01) | |
| H01M 10/0525 | (2010.01) | |
| G01N 27/407 | (2006.01) | |
| H01M 4/02 | (2006.01) | |
| H01M 4/86 | (2006.01) | |

(52) U.S. Cl.
CPC ............. *B01J20/3293* (2013.01); *C01B 31/04* (2013.01); *G01N 27/4075* (2013.01); *H01M 4/1393* (2013.01); *H01M 4/583* (2013.01); *H01M 4/96* (2013.01); *H01M 10/0525* (2013.01); *H01M 2004/027* (2013.01); *H01M 2004/8684* (2013.01)

(56) References Cited

U.S. PATENT DOCUMENTS

| | | | |
|---|---|---|---|
| 4,240,830 A * | 12/1980 | Lee | C04B 35/52 419/28 |
| 4,263,376 A | 4/1981 | Blurton | |
| 4,270,348 A | 6/1981 | Winberg | |
| 4,637,197 A | 1/1987 | Banfield | |
| 4,867,803 A | 9/1989 | Shikata et al. | |
| 5,045,349 A | 9/1991 | Ferrando | |
| 5,478,364 A | 12/1995 | Mitate et al. | |
| 5,882,818 A | 3/1999 | Fujimoto et al. | |
| 6,064,908 A | 5/2000 | Muller et al. | |
| 6,139,990 A | 10/2000 | Kubota et al. | |
| 6,403,259 B1 * | 6/2002 | Kitagawa | H01M 4/0471 429/231.4 |
| 6,528,033 B1 | 3/2003 | Barker et al. | |
| 6,828,064 B1 | 12/2004 | Nardi | |
| 6,949,312 B1 | 9/2005 | Kawakami et al. | |
| 2005/0207966 A1 | 9/2005 | Zaghib | |
| 2010/0028573 A1 | 2/2010 | Lee et al. | |
| 2013/0323600 A1 | 12/2013 | Guerfi et al. | |

FOREIGN PATENT DOCUMENTS

| | | |
|---|---|---|
| EP | 0917228 A1 | 5/1999 |
| EP | 0977292 A2 | 2/2000 |
| JP | 52-146793 A | 12/1977 |
| JP | 52-146793 A | 8/1993 |
| JP | H05-213611 | 8/1993 |
| JP | 10-330107 A | 12/1998 |
| JP | 10-334915 A | 12/1998 |
| JP | 11-31508 A | 2/1999 |
| JP | 11-54123 A | 2/1999 |
| JP | 11-157816 A | 6/1999 |
| JP | 11-263612 A | 9/1999 |
| JP | 11-343108 A | 12/1999 |
| JP | 2000-106182 A | 4/2000 |
| JP | 2000-264614 A | 9/2000 |
| WO | WO 00/17948 A1 | 3/2000 |
| WO | WO 01/62666 A1 | 8/2001 |

OTHER PUBLICATIONS

Zaghib, K., et al., "Thermal analysis of the oxidation of natural graphite: isothermal kinetic studies", Thermochimica Acta 371 (2001), pp. 57-64, Elsevier Science B.V., The Netherlands.

Zaghib, K., et al., "Influence of edge and basal plane sites on the electrochemical behavior of flake-like natural graphite for Li-ion bateries", Journal of Power Sources 97-98 (2001), pp. 97-103, Elsevier Science B.V., The Netherlands.

Zaghib, K., et al., "Effect of Graphite Particle Size on Irreversible Capacity Loss," Journal of the Electrochemical Society, Jun. 2000, vol. 147, No. 6, pp. 2110-2115.

Patent Abstracts of Japan, vol. 2000, No. 12, Jan. 3, 2001 & JP 2000-264614.

Database WPI, Section Ch., Week 199915 & JP 11031508.

International Search Report issued in corresponding PCT/CA01/01511 on May 3, 2002.

Kasuh, T., et al., "Recent Trends in Carbon Negative Electrode Materials", Journal of Power Sources 68 (1997), pp. 99-108, Elsevier Science B.V., The Netherlands.

Osaka, T., et al., "Energy Storage Systems for Electronics", New Trends in Electrochemical Technology, vol. 1, 2000, Gordon and Breach Science Publishers, p. 125.

Salaman, "The Inheritance of Colour and Other Characters in the Potato", Journal of Genetics 1910-1911, 1:7-26.

Kimoto, S., et al., "Stereoscopic Observation in Scanning Microscopy Using Multiple Detectors", pp. 480-489, Japan Electron Optic Laboratory, Tokyo Japan.

Gedecke, D.A., et al., "A Solid Stae Backscattered Electron Detector Capable of Operating at T.V. Scan Rates", vol. 1, 1978, pp. 581-594, Scanning Electron Microscopy.

Definition of Graphite, accessed online @ http://www.thefreedictionary.com/graphite on Oct. 9, 2013.

Fitzer, et al., "Recommended Terminology for the Description of Carbon as a Solid", Pure & Appl. Chem., 1995, 67(3): 473-508.

Dunlap, "Accurate Density-Functional Calculations on Large Systems," International Journal of Quantum Chemistry, 1997, 64:193-203.

Wang, et a., "Lithium insertion/extraction in pyrolyzed phenolic resin", J. Power Sources, 1999, 81-82:328-334.

Yoshio, et al., "Effect of Carbon Coating on Electrochemical Performance of Treated Natural Graphite as Lithium-Ion Battery Anode Material," Journal of the Electrochemical Society 2000, 147(4): 1245-1250.

Office Action issued by the U.S. Patent and Trademark Office in the U.S. Appl. No. 13/617,084, mailed Mar. 28, 2014, U.S. Patent and Trademark Office, Alexandria, VA. (16 pages).

Office Action issued by the U.S. Patent and Trademark Office in the U.S. Appl. No. 13/617,084, mailed Oct. 1, 2014, U.S. Patent and Trademark Office, Alexandria, VA. (22 pages).

* cited by examiner

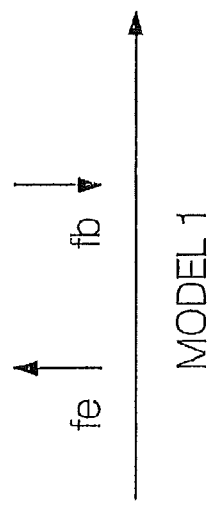
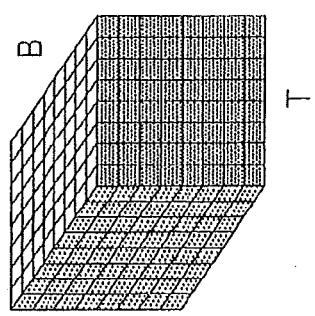
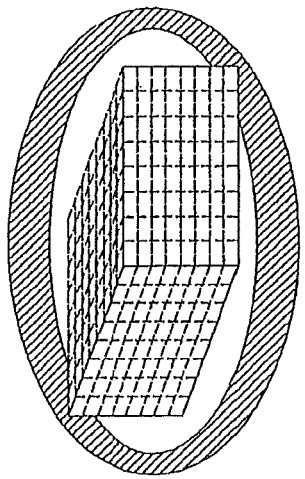
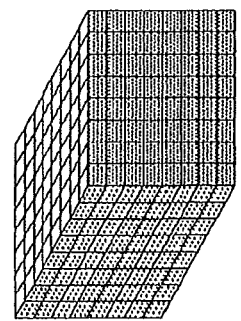
FIG-1

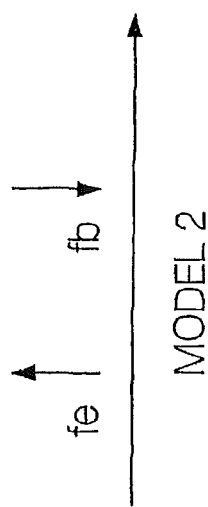
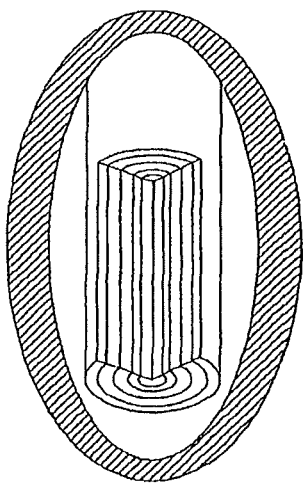
Transition from a cylindrical to a spherical structure
With the exception that fe and fb are constant
Coating by metals, polymers, carbon
The size of the metal layer or of the carbon results in a sphericity > 80%
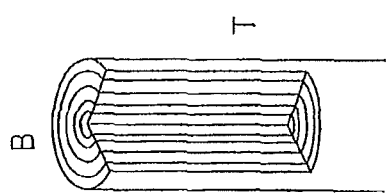
MODEL 2
FIG. 2

Cross-section     Top view     Elementary particle

POTATO-SHAPED GRAPHITE PARTICLES WITH LOW IMPURITY RATE AT THE SURFACE, METHOD FOR PREPARING THE SAME

CROSS REFERENCE TO RELATED APPLICATIONS

This application is a continuation of U.S. application Ser. No. 13/857,861, filed on Apr. 5, 2013, which is a continuation of U.S. application Ser. No. 12/572,510, filed on Oct. 2, 2009, which is a continuation of U.S. application Ser. No. 11/606,231, filed Nov. 30, 2006, which is a continuation of U.S. application Ser. No. 10/381,843, filed Sep. 26, 2003, which was the National Stage of International Application No. PCT/CA01/01511, filed Oct. 24, 2001. This application also claims foreign priority to Canada 2,324,431, filed on Oct. 25, 2000. The entire contents of each U.S. application Ser. No. 13/857,861, U.S. application Ser. No. 12/572,510, U.S. application Ser. No. 11/606,231, U.S. application Ser. No. 10/381,843, International Application No. PCT/CA01/01511, and Canada 2,324,431 of are hereby incorporated herein by reference in their entirety.

TECHNICAL FIELD

The present invention relates to modified graphite particles and to particles based on graphite that are also characterized in that they have a potatolike shape. The present invention also concerns processes that make it possible to prepare these new particles, as well as the use of the particles thus obtained in particular as moisture absorbers and/or oxygen absorbers. These processes can be monitored by controlling the values obtained from the mathematical functions that are characteristic of the shape of the crystalline (edge, basal, Lc and La) and geometric structures of the graphite. These new particles also exhibit, within the scope of an electrochemical application, improved stability to cycling by increasing, on one hand, the density of the electrode and on the other, the diffusion kinetics of the intercaling material (Li, Na or other).

BACKGROUND ART

Graphite has important electrochemical properties. Thus for natural graphites, which are available abundantly in nature, a reversible capacity of 372 mAh/g and a voltage plateau close to that of lithium have been established.

Graphite has been introduced into commercial lithium-ion batteries, as mentioned in the patent granted to Sanyo in the United States, under number U.S. Pat. No. 5,882,818. Its important characteristics, in addition to its low cost price, have made natural graphite a good candidate as anode in lithium-ion batteries. However, coating of uniform electrodes remains problematic due to the physical shape of these particles, which have the shape of flakes. For this reason, carrying out the coating effectively requires an additional calendering step when the electrodes for Li-ion batteries are manufactured (Energy Storage Systems for Electronics, by Testuya Osaka and Madhav Datta, (2000), page 125). The compactness density is low, which results in electrodes having greater thicknesses. The performances of the anode depend on the type of graphite and the physical shape of these particles. The efficiency of the first intercalation of the ion in graphite is dependent on the specific surface area and the edge surface fraction (K. Zaghib et al, J. Electrochemical Soc. 147 (6) 2110 to 2115, 2000). A low specific surface area is associated with a lower contribution of passivation film.

Natural graphite is found exclusively in the form of flakes, while artificial graphite can be found in the form of flakes, fibers or spheres. The flake shape has an elevated degree of preferential orientation which will induce anisotropy in the electrode. An orientation such as this reduces the intercalation kinetics of lithium across the edges. However, the only spherical carbon available on the market is Mesocarbon Microbeads MCMB processed at 2,800° C. by Osaka Gas (T. Kasuh et al., J. Power Source 68 (1997), 99). This carbon is an artificial graphite that requires costly processing at high temperature to be ordered, as well as complex synthesis that can increase its production cost. The maximum reversible capacity obtained with this artificial graphite is of the order of 280 mAh/g, which is low in comparison to the corresponding capacity of natural graphite, which is 372 mAh/g.

U.S. Pat. No. 6,139,990 of Kansai Netsukkagaku Kabushiki Kaisha granted on Oct. 31, 2000, describes graphite particles that are modified and rounded, having an almost spherical form, characterized in that their degree of circularity is greater than or equal to 0.86 and in that, using X-ray diffraction measurement, the peak of the intensity relationship between one face 002 (parallel to the graphite layers) and face 110 (perpendicular to the graphite layers), that serve as the random orientation index, must not be less than 0.0050. These particles have poor homogeneity as regards their granulometric distribution, which limits their use in electrochemical cells, especially with propylene carbonate as electrolyte. This represents a major disadvantage for low-temperature applications. A lack of safety of electrochemical cells incorporating such graphite particles is also noted.

Patent application EP-A-0,916,618 filed in the name of the OSAKA GAS Co. Ltd., on the other hand, describes a graphite material in which the formation of cavities has been optimized in order to increase the electrochemical capacity of the electrodes containing it. While these materials have become interesting with regard to their use in primary-type batteries, they are of little interest for other electrochemical applications, in particular because of the fragility of their structure and the resulting lack of stability for capacities greater than 400 mA/g.

The handling required for converting natural graphite into spherical graphite presents net advantages in comparison to the standard natural graphite present in the form of flakes, as well as in comparison to spherical artificial graphite (MCMB).

Thus a need existed for graphite-based particles in a stable form that can be compressed easily to the point of obtaining an elevated density, these particles presenting electrochemical capacities and anisotropies that are greater than or equal to those of the known forms of graphite particles. In particular, these particles make it possible to produce homogeneous and compact electrodes and also promote the use of PC.

SUMMARY OF THE INVENTION

The present invention especially concerns potatolike shaped modified graphite particles having impurities in their internal structure and having on the surface a low, even nil, rate of an impurity or several impurities, in particular the impurities usually present in natural graphites.

The present invention also relates to particles based on modified graphite made up of prismatic graphite particles covered with a metallic deposit and/or a carbonic deposit.

The graphite particles according to the present invention can be used, in particular, as humidity absorbers and/or oxygen absorbers and, especially because of their cycling performance, can be used in the manufacture of negative electrodes, preferably in the manufacture of negative electrodes for rechargeable electrochemical generators.

The present invention also concerns methods that make possible the preparation of these particles and the preparation of electrodes containing them.

BRIEF DESCRIPTION OF DRAWINGS

FIG. 1: According to model 1, transformation of the prismatic particles into spherical particles by decreasing the fb and increasing the fe. This transformation can be carried out using several techniques: jet mill, attrition, ball mill, hammer mill, CF mill or atomizer mill, planetary mixer, hybridizer.

According to model 1, transformation of the prismatic particles into spherical particles by keeping fe and fb constant. This transformation is carried out by coating the particles with a metal, polymer or carbon.

FIG. 2: According to model 2, transformation of the cylindrical particles into spherical particles by decreasing the fb and increasing the fe. This transformation can be carried out using several techniques: jet mill, attrition, ball mill, hammer mill, CF mill or atomizer mill, planetary mixer, hybridizer.

According to model 2, transformation of the prismatic particles into spherical particles by keeping fe and fb constant. This transformation is carried out by coating the particles with a metal, polymer or carbon.

Figure 3:
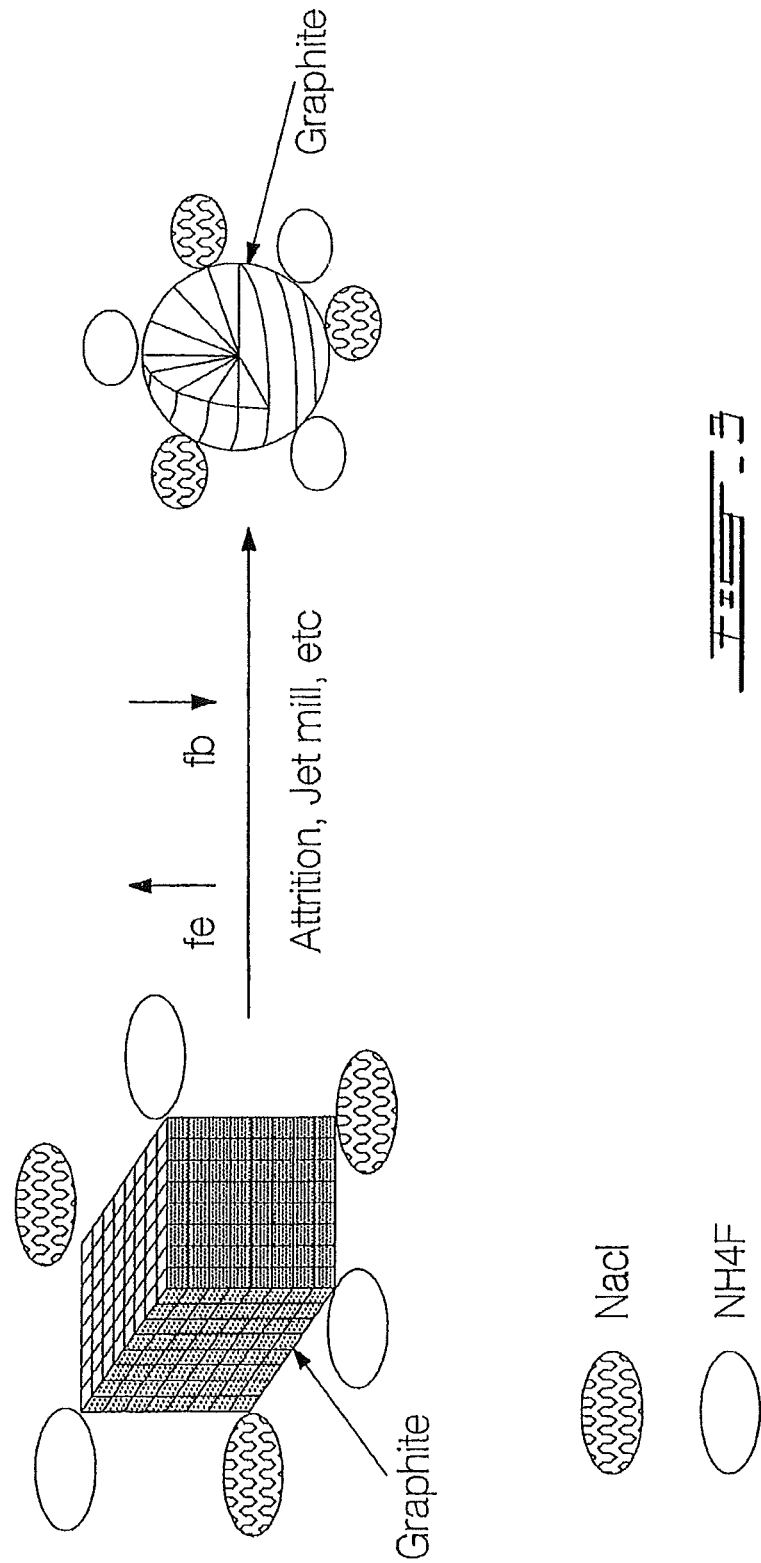

FIG. 3: According to model 1, the prismatic-shaped artificial or natural graphite, in the presence of its impurities and soluble agents of the NaCl and $NH_4F$ type or the like (preferably with spherical shape), is transformed into spherical-shaped graphite by decreasing the basal fraction (fb) and increasing the edge fraction (fe). This transformation can be carried out using several techniques: jet mill, attrition, ball mill, hammer mill, CF mill or atomizer mill, planetary mixer, hybridizer.

Figure 4:
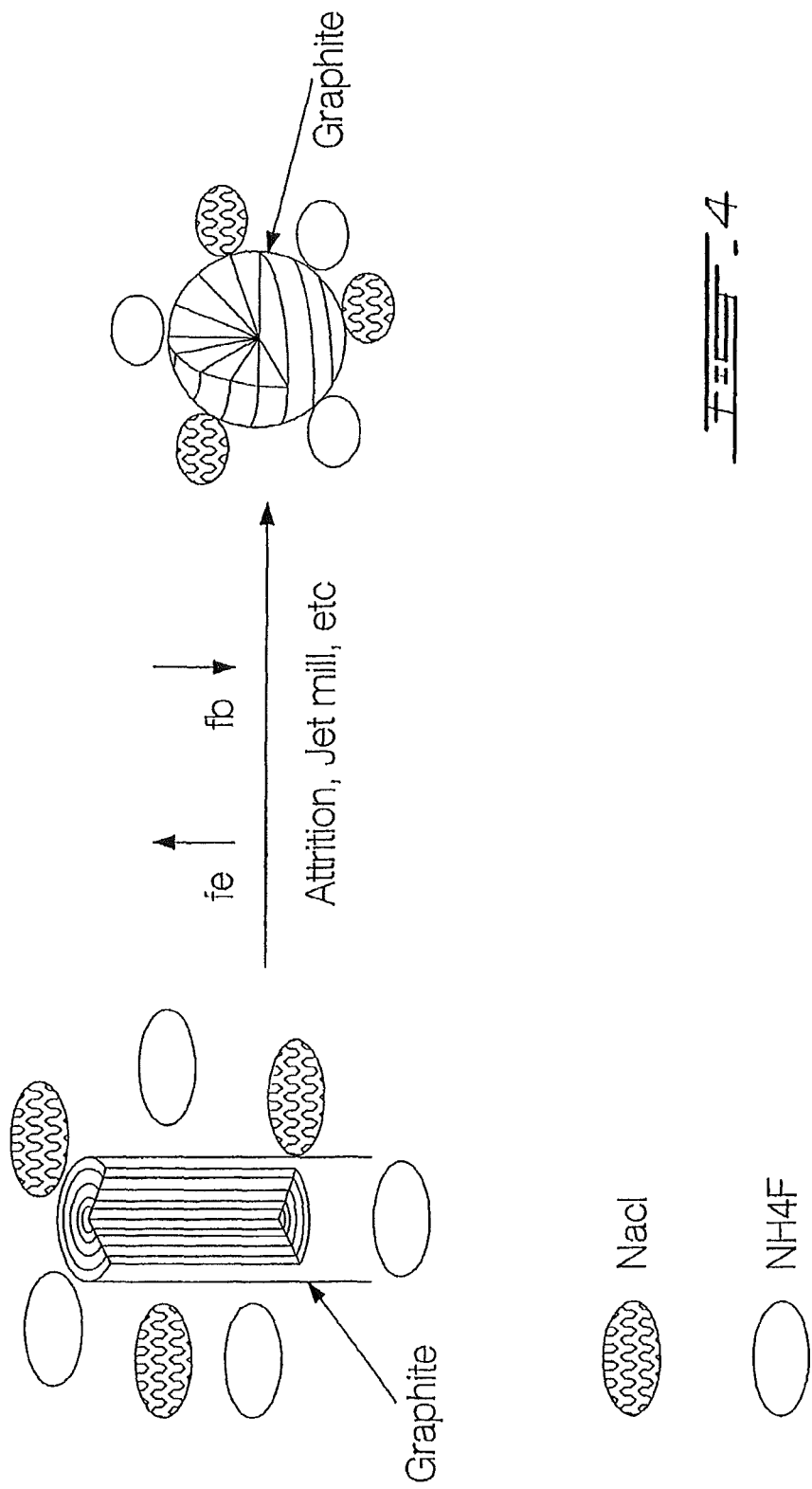

FIG. 4: According to model 2, the carbon fiber, the cylindrical-shaped artificial or natural graphite, in the presence of its impurities and soluble agents of the NaCl and $NH_4F$ type or the like (preferably with spherical shape), is transformed into spherical-shaped graphite by decreasing the basal fraction (fb) and increasing the edge fraction (fe). This transformation can be carried out using several techniques: jet mill, attrition, ball mill, hammer mill, CF mill or atomizer mill, planetary mixer, hybridizer.

Figure 5:
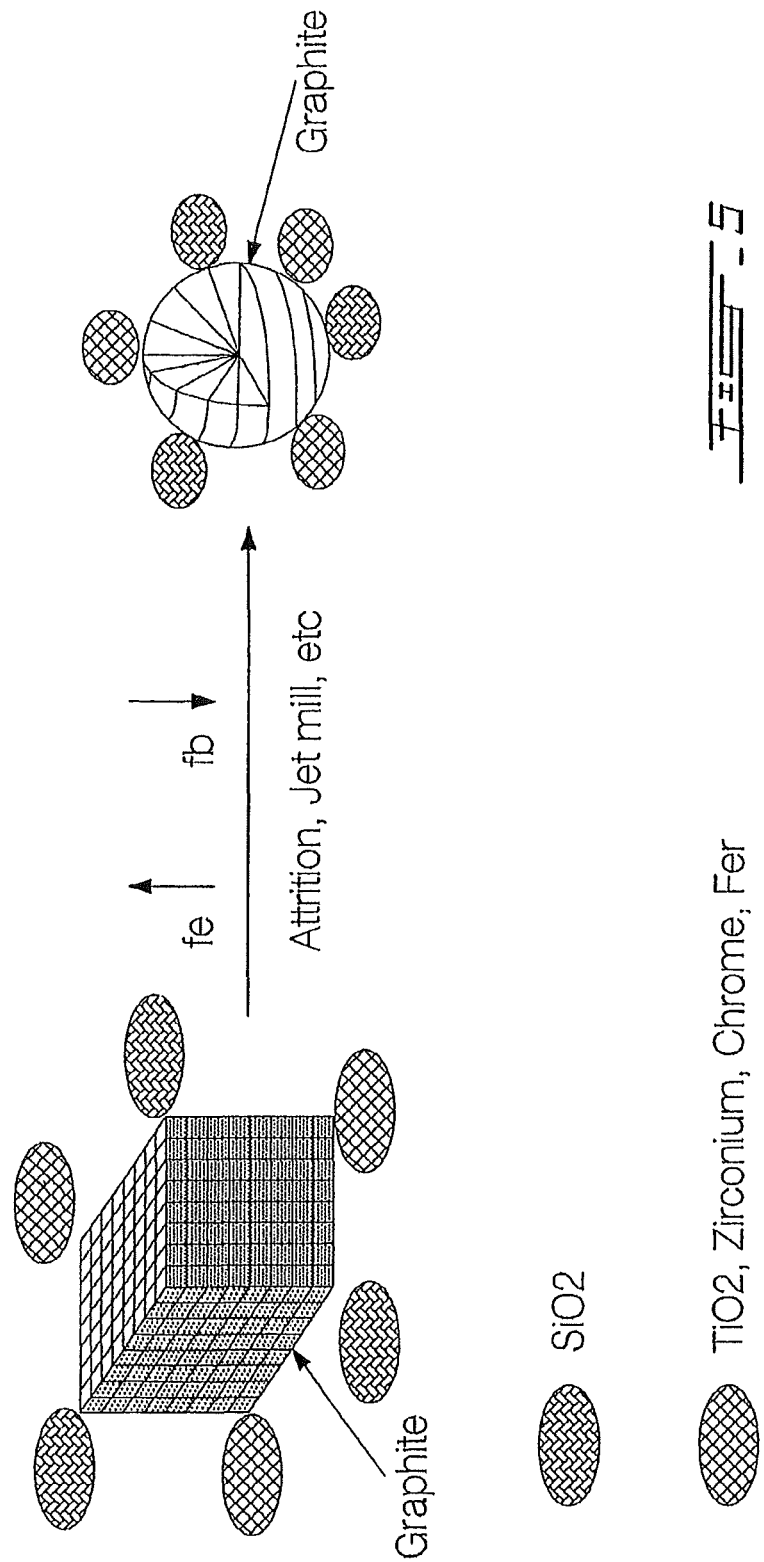

FIG. 5: According to model 1, the prismatic-shaped artificial or natural graphite, in the presence of its impurities and non-soluble agents of the $SiO_2$ and $TiO_2$ type, ceramic material, hard compound or the like (preferably with spherical shape) is transformed into spherical-shaped graphite by decreasing the basal fraction (fb) and increasing the edge fraction (fe). This transformation can be carried out using several techniques: jet mill, attrition, ball mill, hammer mill, CF mill or atomizer mill, planetary mixer, hybridizer.

Figure 6:
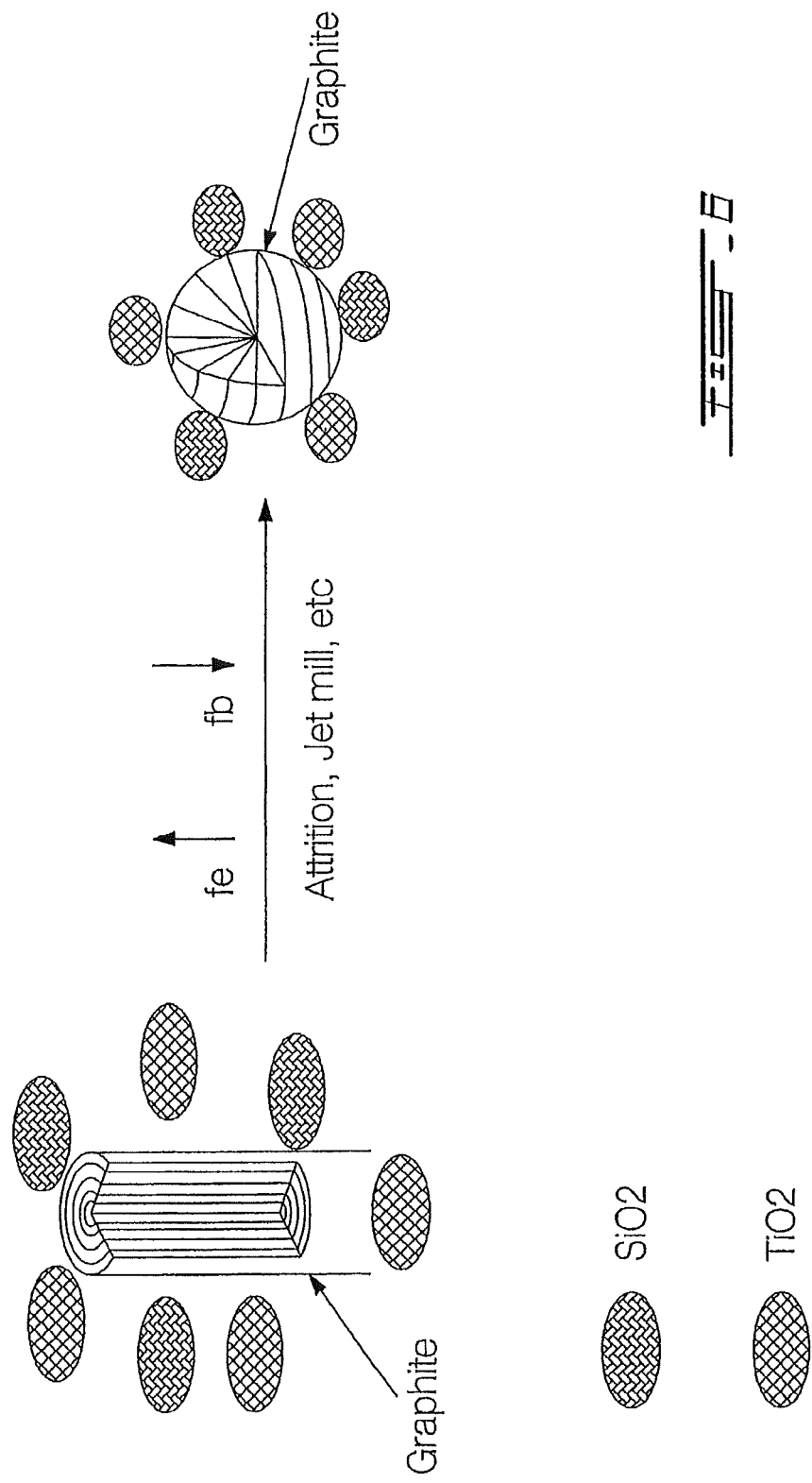

FIG. 6: According to model 2, the cylindrical-shaped artificial or natural graphite, in the presence of its impurities and non-soluble agents of the $SiO_2$ and $TiO_2$ type, ceramic material, hard compound or the like (preferably with spherical shape), is transformed into spherical-shaped graphite by decreasing the basal fraction (fb) and increasing the edge fraction (fe). This transformation can be carried out using several techniques: jet mill, attrition, ball mill, hammer mill, CF mill or atomizer mill, planetary mixer, hybridizer.

Figure 7:
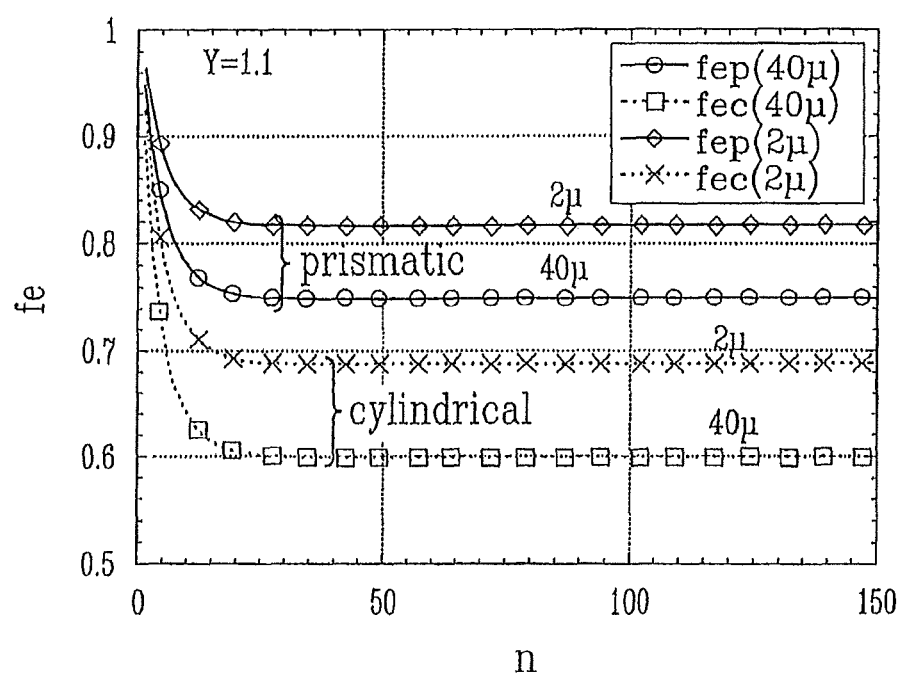

FIG. 7: Comparative modeling between the prismatic and cylindrical model for two types of particles of 2 and 40 μm.

Figure 8:
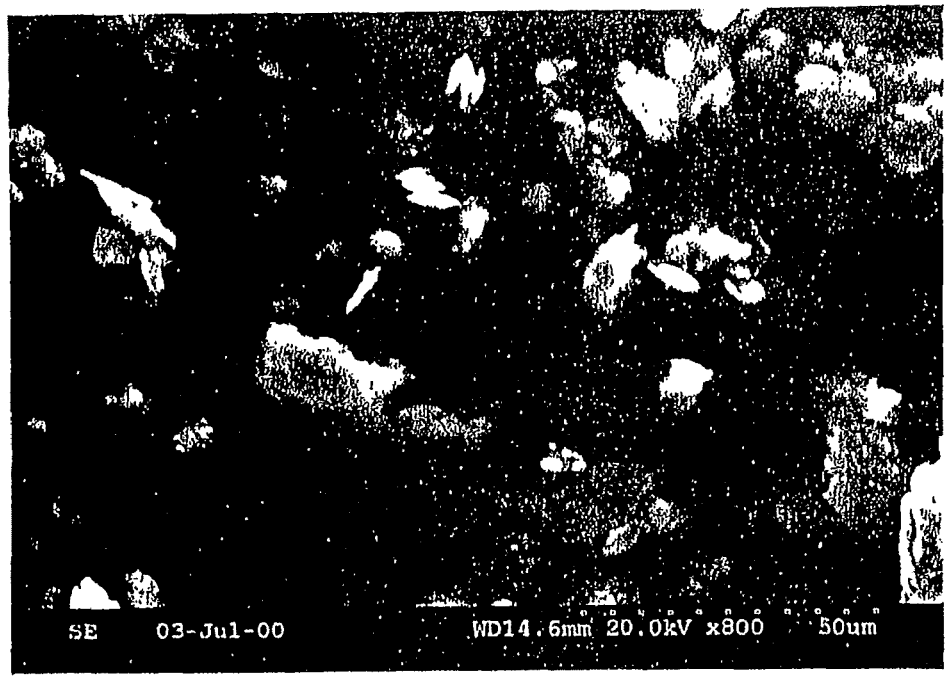

FIG. 8: Graphite particles before attrition.

Figure 9:
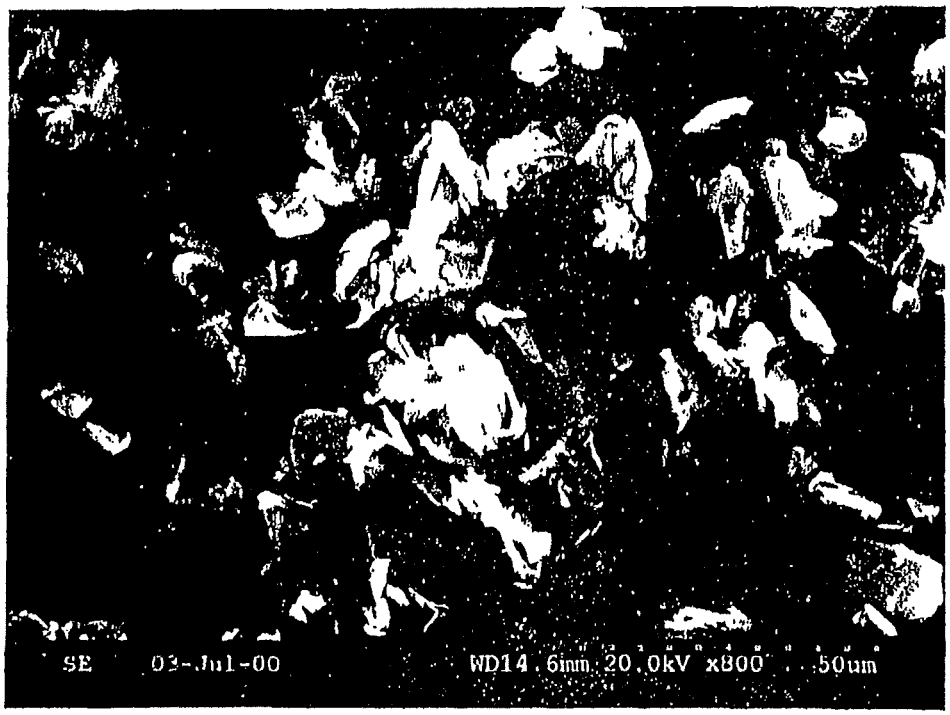

FIG. 9: Graphite particles after attrition.

Figure 10:
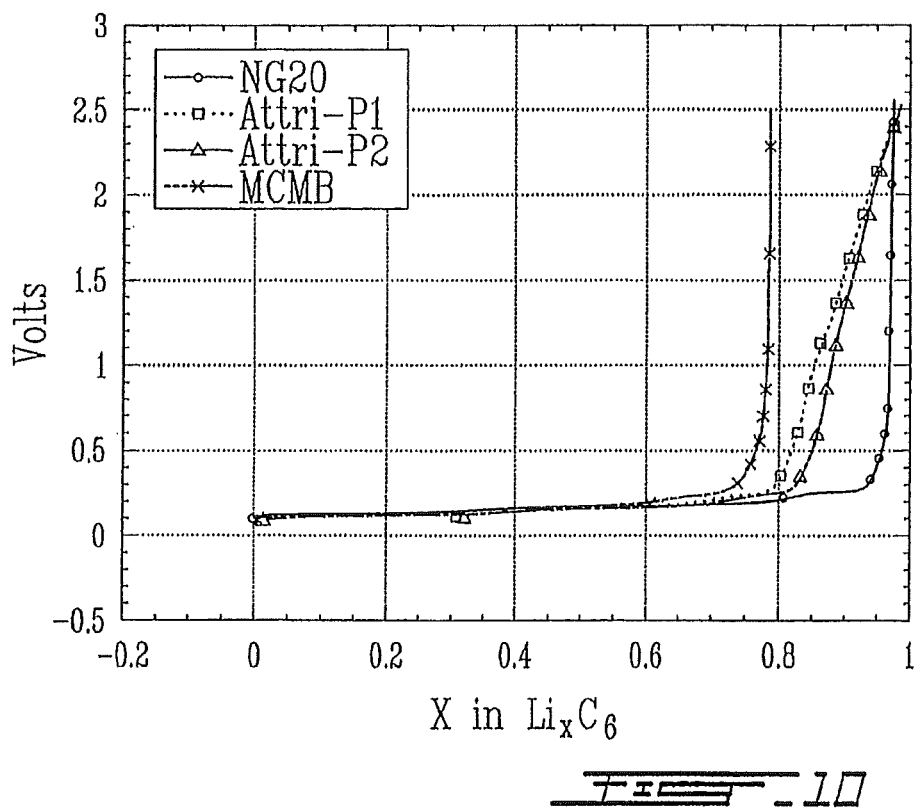

FIG. 10: Electrochemical results of natural graphite NG20, after attrition.

Figure 11:
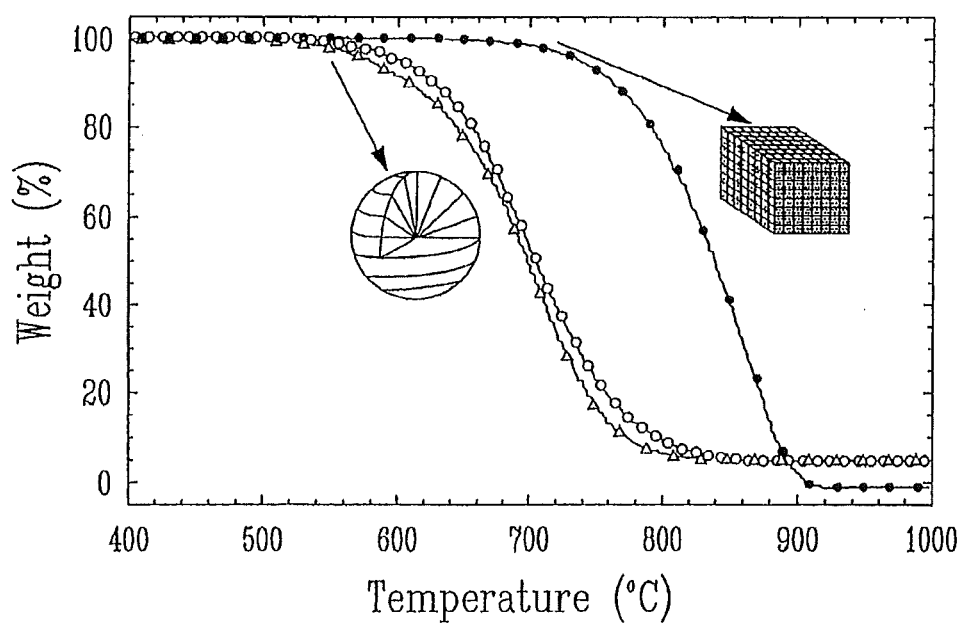

FIG. 11: Electrochemical results with commercial spherical graphite MCMB.

Figure 12:
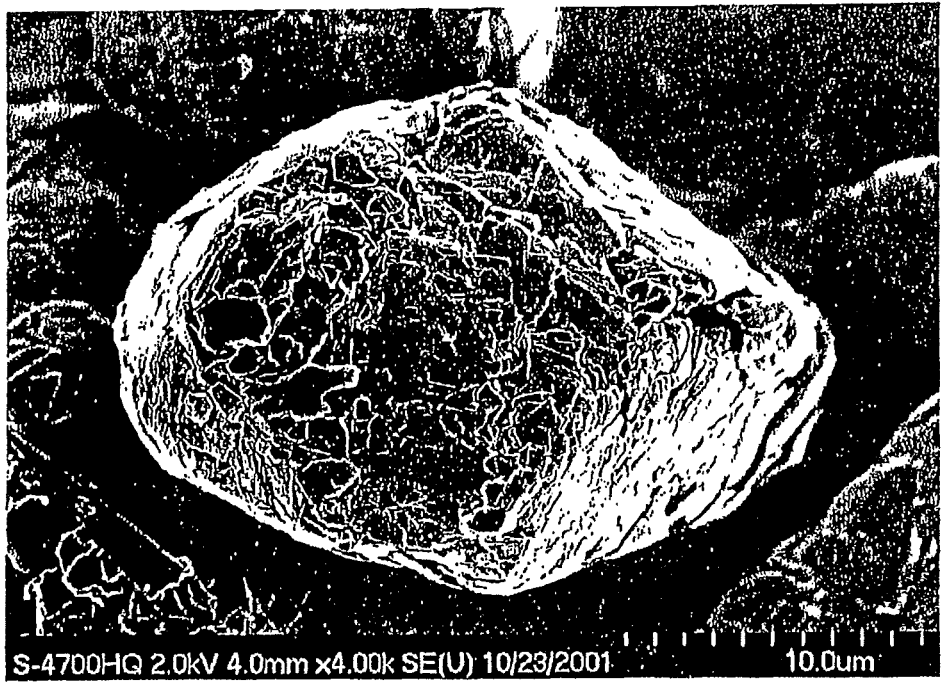

FIG. 12: Scanning electron microscope micrograph showing the potatolike shape of a 12 μm particle obtained in example 3, according to the invention.

Figure 13:

FIG. 13: Scanning electron microscope (MEB) micrograph showing the trend in basal and edge functions for a graphite particle conforming to mathematical model 1.

Figure 14:
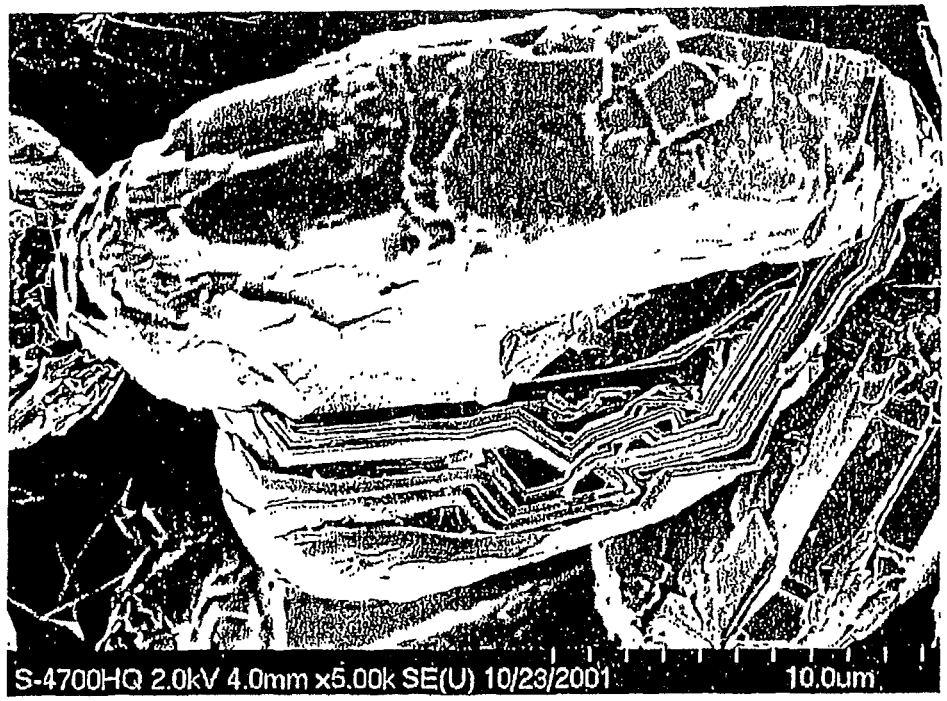

FIG. 14: Scanning electron microscope micrograph showing the potato shape of a 12 μm graphite particle obtained in example 3.

Figure 15:
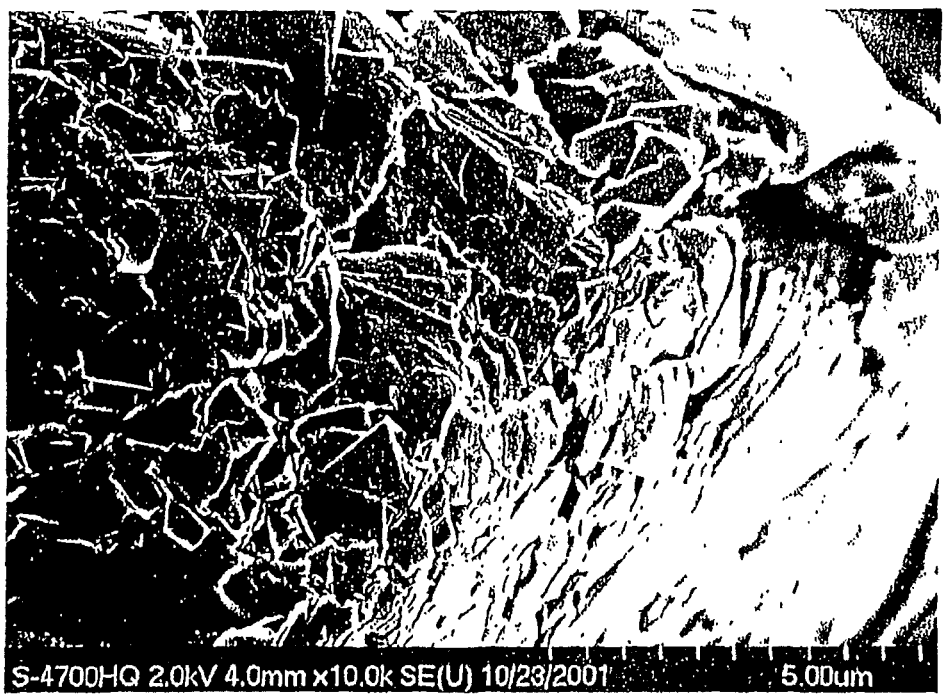

FIG. 15: Micrograph of a particle obtained in example 3, micrographed with the scanning electron microscope (MEB), showing that the basal function (fb) decreases and the function (fe) increases.

Figure 16:
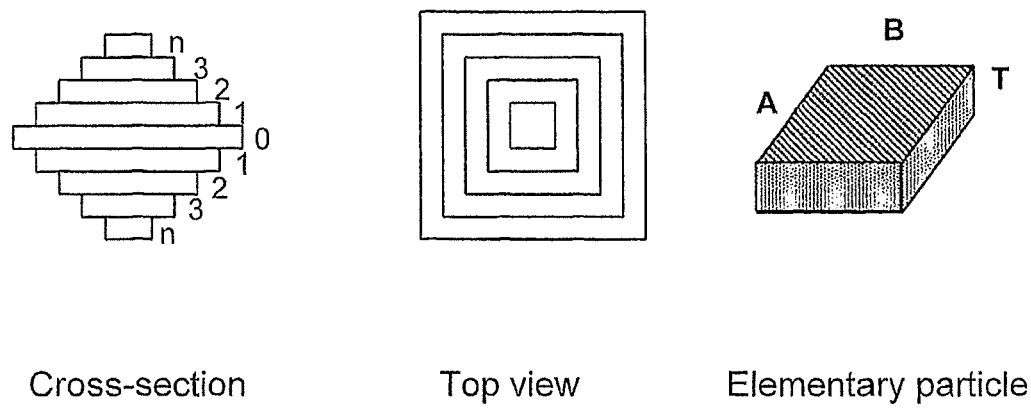

FIG. 16: Exemplary particle showing a central layer (0) toward peak (n) or toward base (n) of the particle.

Figure 17:
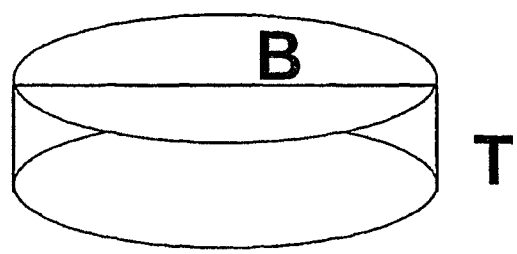

FIG. 17: Exemplary graphite particle is formed by elementary cylindrical particles with a diameter B and a thickness T.

MODES OF CARRYING OUT THE INVENTION

A first object of the present invention comprises modified graphite particles obtained from graphite (preferably from synthetic graphite), the structural parameters of said particles corresponding to at least one of the equations $$fe_1=[Y+1]/[(Y+1)+(B/2T)(Y-1)] \text{ and } fe_2=[Y+1]/[(Y+1)+(B/T)(Y-1)],$$

where Y represents a whole number greater than or equal to 1, B represents the length of the particle in μm, T represents the thickness of the particle in μm. These particles also have a potatolike shape and have at least one of the following two characteristics:

a tap density, measured according to the method associated with the instrument sold under the name of Logan Instrument Corp. Model Tap-2, between 0.3 and 1.5, preferably between 0.5 and 1.4, most preferably between 1 and 1.3 g/cc; and a granulometric dispersion measured according to the method associated with the particle analyzer sold under the name Microtac Model X100 Particle Analyzer, such that the D90/D10 distribution ratio varies between 2 and 5 and the particles have a size between 1 μm and 50 μm, preferably such that the D90/D10 distribution ratio varies between 2.2 and 4.2 and the particles have a size between 2 μm and 30 μm.

A second object of the present invention comprises modified graphite particles obtained from graphite, said particles having a potatolike shape, comprising impurities in their internal structure and having on the surface a rate of one or more impurities, measured according to the retrodiffused detector method defined in the publication Kimoto S. and Hashimoto H., (1966), in Electron Microphone, John Wiley, New York, page 480 and in Gedcke, D. A., Ayers, J. B. and DeNee, P. B. (1978), SEM/1978, SEM Inc, AMF O'Hare, Ill., page 581, that is less than 10%, which preferably varies between 2% and 4%, and said particles also having at least one of the following three characteristics:

a tap density measured according to the previously identified method between 0.3 and 1.5, preferably between 0.5 and 1.4, most preferably between 1 and 1.3 g/cc;

a granulometric dispersion measured according to the previously identified method, such that the D90/D10 ratio varies between 2.2 and 4.2 and the particles have a size between 2 and 30 µm; and they have, attached to their surface, particles (preferably potatolike shape, most preferably spherical) of NaCl and/or $NH_4F$; preferably the mass of these particles of NaCl and/or of $NH_4F$ represents 1 to 4% of the total mass of the modified graphite particles.

The rate of impurities on the surface of graphite may be reduced in different ways; one particularly effective method is the one described in the application PCT/CA100233 held by the Hydro-Québec Company. The contents of this document are incorporated in the present application by reference.

A preferred sub-family of the particles according to the second object of the present application is made up of modified graphite particles for which TGA analysis carried out according to the method associated with the device sold under the name TGA/DTA Model SDT 2960, TA Instruments Inc., New Castle, Del., gives an initial temperature value between 560 and 660 degrees Celsius, associated with the loss of weight, as is illustrated in FIG. 11.

The particle parts of graphite modified according to the invention may contain impurities, for example, at least one impurity from the group made up of the chemical elements Fe, Mo, Sb, As, V, Cr, Cu, Ni, Pb, Co, Ca, Al, Ge, Si, Ba, Be, Cd, Ce, Co, Cu, Dy, Eu, La, Li, Mo, Nd, Ni, Pb and Pr.

One preferred sub-family among the graphite particles according to the invention is made up of particles in which the percentage of impurities by weight present in the said particles, expressed with respect to the total mass of modified graphite particles and measured according to the ash method, is between 1 and 10%, and preferably between 2 and 4%.

More especially interesting are the graphite particles according to the invention that are substantially lacking in surface impurities and preferably those devoid of surface impurities.

A third object of the present invention comprises modified graphite particles obtained from graphite, said particles having a potatolike shape and containing from 5 to 20% of at least one of the following compounds $SiO_2$, MgO, ceramic compounds or a mixture of these, said compounds preferably being attached to the modified graphite particles by physical forces and having at least one of the following three characteristics:

a tap density measured according to the previously described method between 0.3 and 1.5, preferably between 0.4 and 1.4, most preferably between 1 and 1.3 g/cc;

a granulometric dispersion measured according to the previously defined method, such that the D90/D10 ratio varies between 2 and 5 for particles with a size between 1 and 50 µm, preferably such that the D90/D10 ratio varies between 2.2 and 4.2 for particles having a size between 2 and 30 µm; and they have, attached to their surface, particles (preferably potatolike shaped, most preferably spherical) of NaCl and/or of $NH_4F$; preferably the mass of these particles of NaCl and/or of $NH_4F$ represents 1 to 10% of the total weight of the modified graphite particles.

One particularly advantageous family of graphite particles according to the present invention is made up of all the modified graphite particles in which the interplane distance $d_{002}$ (measured according to the method associated with the diffractometer sold under the name XRD Analysis Siemens Model D500 Diffractometer) varies from 33 to 3.4 angstroms and/or the BET (measured using the method associated with the device Quantachrome Autosorb automated gas adsorption system using $N_2$) varies between 0.5 g/m² and 50 g/m².

Among the modified graphite particles of the invention, those having a cycling stability greater than 500 cycles are of particular interest in the scope of electrochemical applications.

A fourth object of the present invention comprises a process for preparing graphite particles (preferably from natural graphite) that are the object of the present invention by using at least one physical means that makes possible the reduction of at least 50% of the basal function (fb) and the increase of at least 50% of the edge function (fe) of the graphite particles, such physical means preferably being attrition, a jet mill, ball mill, hammer mill, atomizer mill, in the presence of at least one chemical compound selected from the group made up of compounds of the formula $MF_z$, in which M represents an alkaline or alkaline-earth metal and z represents 1 or 2 (preferably MFz represents $CaF_2$, $BaF_2$, LiF), NaCl and $NH_4F$ or a mixture thereof, said compound or compounds preferably being added in solid form, preferably at the beginning of the step using the physical means that makes it possible to reduce the basal function defined by the equation fb=1−fe and to increase the function fe defined by the ratio $(2B/La+T/d_{002})$: $(2B/d_{100}+T:d_{002})$ in which B is the length of the particle, $La=d_{100}(2n+1)$ represents $d_{002}$, n represents a number of planes. These functions are defined and analyzed in detail in the publication Effect of Graphite Particle Size on Irreversible Capacity Loss, K. Zaghib, G. Nadeau, and K. Kinoshita, Journal of the Electrochemical Society 147 (6) 2110-2115 (2000). This document is incorporated into the present application in its entirety by reference.

As described in application PCT/CA0100233 of Hydro-Québec, the use of $NH_4F$ on the surface the graphite at the time of grinding is very important since $NH_4F$, at the time of the purification of graphite in the presence of $H_2SO_4$ and $H_2O$, generates HF to dissolve the impurities, in particular $SiO_2$.

In the same way, the use of NaCl on the surface of graphite at the time of grinding is very important, since, at the time of the purification of graphite in the presence of $H_2SO_4$, NaCl generates HCl which also dissolves the impurities on its surface, in particular the metals Fe, Mo and the like.

According to an advantageous mode of using the method, the reduction of the basal function and the increase of the edge function, preferably the rounding of the particles, is carried out using a means of attrition, said means preferably being made up of balls such as steel balls, ceramic balls or a mixture of steel and ceramic balls.

A fifth object of the present invention comprises a process for preparing modified graphite particles according to claim 1 or 2, preferably from natural graphite, comprising at least the following two steps:

i) modification of the shape of the graphite particles by using at least one physical means making possible the reduction of at least 50% of the basal function (fb) and the increase of at least 50% of the edge function (fe) of synthetic graphite particles (preferably of natural graphite), such physical means preferably being attrition (preferably a jet mill, ball mill, hammer mill, an atomizer mill) in the presence of at least one chemical compound selected from the group consisting of compounds of the formula $MF_z$, in which M represents an alkaline or alkaline-earth metal and z represents 1 or 2, $MF_z$ preferably represents $CaF_2$, $BaF_2$, LiF or a mixture thereof, the compound or compounds preferably being added in solid form, preferably at ambient temperature, preferably at the beginning of the step using the means that make possible the reduction of the basal function and the increase of the edge function; and ii) reduction in the amount of surface impurities, preferably by purification, preferably by chemical purification of the graphite particles obtained in step i).

According to an advantageous embodiment, the graphite particles used at the beginning of the process have a size between 1 and 450 μm, preferably between 2 and 350 μm.

According to another advantageous embodiment, the attrition process is carried out in the presence of an additive, preferably an additive of the metallic oxide type such as $SiO_2$, $TiO_2$, $ZrO_2$, and preferably in the presence of steel balls, ceramic balls or in the presence of a mixture of steel and ceramic balls.

A preferred variation comprises using the method according to the invention under conditions such that at least one of the two steps is carried out in a controlled atmosphere or in air, the controlled atmosphere preferably being based on nitrogen, argon, helium or a mixture of these gases.

Step i) can be a hybrid step using both jet milling and attrition, the attrition preferably being carried out after jet milling is used.

According to a particularly advantageous method, step i) of the method is carried out using jet milling.

A sixth object of the present invention comprises modified graphite particles such as defined above and below, as moisture sensors and/or oxygen absorbers.

A seventh object of the present invention comprises negative electrodes, preferably negative electrodes for a rechargeable electrochemical generator prepared with a bonding agent, preferably a bonding agent of the PVDF or PTFE type, and with graphite particles according to any one of the objects of the present invention.

An eighth object of the present invention is made up of a process for preparing an electrode for a rechargeable generator based on graphite particles according to the present invention or based on graphite particles such as those obtained by a method according to the invention, comprising at least the following steps:

a—solubilization of at least one bonding agent (preferably selected from the group comprising PVDF, PTFE) in a solvent (preferably in a strong solvent selected from the group comprising NMP (N-methylpyrrolidone), cyclopentanone at the highest possible concentration (preferably greater than 1 g/cc)) to obtain a viscous solution (A);

b—coating the viscous solution obtained in the preceding step, which is a powder-bonding agent compound (B), on a device of the collector type, preferably on a collector of the metallic type and/or of the perforated metal collector type, said collector thus treated making up an electrode; and c—drying the electrode prepared in step b); the drying preferably being carried out using an infrared lamp or using a heating element.

According to a preferred embodiment of this method, in step c) two distinct means are used in parallel to dry the electrode, these means preferably being drying by infrared lamp and drying by heating element.

A ninth object of the present invention is made up of modified graphite-based particles that are made up of prismatic particles of graphite covered with a metallic deposit and/or a carbonic deposit, the structural parameters of said particles corresponding to the equations $fe_1=[Y+1]/[(Y+1)+(B/2T)(Y-1)]$ and $fe_e=[Y+1]/[(Y+1)+(B/T)(Y-1)]$, in which: Y represents a whole number greater than or equal to 1, B represents the length of the particle in μm, T represents the thickness of the particle in μm, said particles having a potato-like shape and having at least one of the following two characteristics:

a tap density measured according to the previously defined method, preferably between 0.3 and 1.5, more preferably between 0.5 and 1.4, and most preferably between 1 and 1.3 g/cc; and a granulometric dispersion measured according to the previously defined method, such that the D90/D10 ratio varies between 2 and 5 and the particles have a size between 1 and 50 μm, preferably such that the D90/D10 ratio varies between 2.2 and 4.2 and the particles have a size between 2 and 30 μm.

Preferably the size of these graphite-based particles is between 1 and 50 μm.

According to an advantageous embodiment, these particles have a sphericity of 80% or more.

Among all of these graphite-based particles, a preferred sub-family is made up of particles in which the average thickness of the metallic and/or carbonated coating is between 50 nm and 2 μm.

Another preferred sub-family is made up of graphite-based particles made up of a coated graphite core, said core making up at least 90% by weight of the total mass of the graphite-based particle, the remaining 10% preferably being made up of at least one metal selected from the group comprising Ag, Si, Al and Cu and/or carbon and/or a carbonated polymer, preferably in prismatic or fiber form.

A tenth object of the present invention comprises a process for preparing the graphite-based particles using prismatic-shaped particles, by coating the particles while keeping the basal function (fb) and the edge function (fe) constant while wrapping the graphite surface with a metallic or carbonic deposit in such a way as to obtain a sphericity of 80% or more.

An eleventh object of the present invention comprises a (preferably) in situ process for purifying the surface of graphite particles, by coating these particles, in the presence of their impurities, with carbon.

A twelfth object of the present invention comprises the use of modified graphite particles according to the invention in an electrochemical cell, with a control of the basal function (fb) that permits their use in the presence of an electrolyte based on polyethylene carbonate (PC), the concentration of PC in the electrolyte then being less than 50% by volume of the electrolytic mixture.

The safety batteries resulting from this utilization also make up an object of the present invention.

A thirteenth object of the present invention is made up of the use of the graphite-based particles according to the invention with a constant basal function (fb) which makes possible their use in the presence of an electrolyte based on polyethylene carbonate (PC), up to a PC concentration in the electrolyte that is then less than or equal to 100% by volume of the electrolytic mixture. The batteries resulting from this utilization are safe and make up an object of the present invention.

Thus within the scope of the present invention, in particular, a new method for transforming the natural graphite particles into spherical particles is described. The coarse graphite powder, in the presence of these impurities that play a microabrasive role (HQ patent), having initial particles of 375 μm, is subject to grinding by attrition in order to reduce its size to a $d_{50}$ of 10 μm. Steel balls are added to the graphite powder in a weight ratio of 1:10 graphite: balls. Grinding (ATTRITOR, type B, size S Union Process Inc, AKRON) is accelerated to a speed of 400 rpm for 60 minutes. After 60 minutes, the grinding is stopped and an evaluation of the granulometry and of the specific surface area is carried out on the sample. If the desired granulometric distribution is not achieved, the grinding is repeated for a period of 10 minutes. These steps will be continued until a $d_{50}$ of 10 µm is obtained. A second 500 g sample is ground in an Alpine jet air grinder to obtain a $d_{50}$ of 10 µm. A comparative study using scanning microscopy is carried out on the two samples after grinding. This allows us to identify whether the shape of the flakes obtained by attrition comes closer to that of a sphere. We have also used hybrid grinding; the size of the particle is reduced first to 20 µm by jet milling, then the particle is sized to 10 µm using attrition.

The use of spherical graphite as anode in a rechargeable battery configuration has many advantages in comparison to graphite in flakes, in particular:
   the density of the consistency is increased;
   the coating is more uniform;
   the porosity is reduced;
   the fraction of basal planes is reduced;
   better inter-particle electrical contact;
   decomposition of the electrolyte is reduced;
   a rapid charge-discharge rate;
   the intercalation kinetics are better; and
   the safety of the battery is improved.

Application of this process to natural graphite improves its electrochemical performance and its use for coating the electrode. Natural graphite made into spherical form combines the advantages of the two carbons: those of natural graphite and those of spherical artificial graphite. The energy is maintained at its maximum with natural graphite (average capacity and voltage). The contribution of the basal planes is reduced, which promotes on the one hand the reduction in irreversible capacity due to passivation and the increase of diffusional parts (edges) along the crystallographic axis C (perpendicular to the planes formed by the carbon atoms). In addition, the problem of anisotropy is reduced and the intercalation kinetic is improved. Spherical particles make coating of the electrodes more homogeneous and make the electrodes obtained less porous. The thickness of the electrodes with spherical particles is better controlled and can achieve smaller thicknesses for power applications, such as pulses for telecommunication and power take-offs for hybrid vehicles. These characteristics facilitate the design of super-thin Li-ion batteries up to the level of polymer batteries.

Calculation models of the relationship between the graphite particles and their surfaces (basal and edge): comparison between the prismatic and spherical structure.

Model I

A mathematical model for the spherical particle has been developed in order to express the relationship between the size of the graphite crystallite and the sites on the surface by using crystallographic parameters a, b and c. In this model, it is assumed that the sphere is formed of prismatic layers with dimension Ai.Bi (basal plane) and thickness T (edge) stacked on each other.

It is also assumed that parameters A and B are smaller by the same factor (Y) as they move away from the central layer (0) toward peak (n) or toward base (n) of the particle (FIG. 16).

Central layer (0): A, B, T
Layer (1):
$A_1$, $B_1$, T where $A = Y A_1$, $B = Y B_1$ and Y 1

$$A_1 = A/Y, B_1 = B/Y \quad (1)$$

Layer (2):
$A_2$, $B_2$, T where $A_1 = Y A_2$, $B_1 = Y B_2$ $$A_2 = A_1/Y = A/Y^2, B_2 = B_1/Y = B/Y^2 \quad (2)$$

Layer (3):
$A_3$, $B_3$, T where $A_2 = Y A_3$, $B_2 = Y B_3$ $$A_3 = A_2/Y = A/Y^3, B_3 = B_2/Y = B/Y^3 \quad (3)$$

.
.
.

Layer (n):
$A_n$, $B_n$, T where $A_{n-1} = Y A_n$, $B_{n-1} = Y B_n$ $$A_n = A_{n-1}/Y = A/Y^n, B_n = B_{n-1}/Y = B/Y^n \quad (4)$$

Thus, for the surface of the edge:

$$EA = 2T[(A+B) + (A_1+B_1) + (A_2+B_2) + (A_3+B_3) + \ldots + (A_n+B_n)] \quad (5)$$

By substitution of the values of $A_1, B_1, A_2, B_2, \ldots, A_n, B_n$ of equations 1, 2, 3 and 4 in 5;

$$EA = 2T(A+B)[1 + 1/Y + 1/Y^2 + 1/Y^3 + \ldots + 1/Y^n]$$

$$= 2T(A+B)\Sigma 1/Y^i \quad (i=0 \text{ to } n) \quad (6)$$

Considering the symmetry of the sphere, equation (6) will take the form:

$$EA = 4T(A+B)[\Sigma 1/Y^i] - 2T(A+B), (i=0 \text{ to } n) \quad (7)$$

The series $[\Sigma 1/Y^i]$ (i=0 to n) converges toward the term $Y/(Y-1)$
(mathematic table $1 + x + x^2 + \ldots + x^n = 1/(1-x)$, where $1 < x < 1$)

$$EA = 4T(A+B)Y(Y-1)^{-1} - 2T(A+B)$$

$$EA = 2T(A+B)[2Y(Y-1)^{-1} - 1] \quad (8)$$

For the surface of the basal planes:

$$BA = 2[(AB - A_1 B_1) + (A_1 B_1 - A_2 B_2) + (A_2 B_2 - A_3 B_3) + \ldots (A_{n-1} B_{n-1} - A_n B_n)]$$

$$= 2[AB - A_n B_n]$$

$$= 2AB[1 - 1/Y^{2n}]$$

$$BA = 2AB[1 - 1/Y^{2n}] \quad (9)$$

The total surface area will be:

$$S_t = EA + BA$$

$$= 2T(A+B)[2Y(Y-1)^{-1} - 1] + 2AB[1 - (1/Y^{2n})]$$

The fraction of the edge sites ($f_e$);

$$f_e = EA/S_t$$

$$= 2T(A+B)[2Y(Y-1)^{-1} - 1]/[2T(A+B)[2Y(Y-1)^{-1} - 1] + 2AB[1 - (1/Y^{2n})]]$$

$$f_e = [Y+1]/[(Y+1) + [AB/T(A+B)][1 - (1/Y^{2n})](Y-1)] \quad (10)$$

When A=B;

$$f_e = [Y+1]/[(Y+1) + (B/2T)(1 - Y^{-2n})(Y-1)] \quad (11)$$

1) in an ideal case, when $n \to \infty$, $Y^{-2n} \to 0$;
(when an infinite number of prismatic layers are considered)

$$f_e = [Y+1]/[(Y+1) + (B/2T)(Y-1)] \quad (12)$$

equation (12) expresses the relationship between the surface of the edges as a function of the dimensions of the particle and of parameter Y.

Model 2

If it is considered that the approximation of the graphite particle is formed by elementary cylindrical particles with a diameter B and a thickness T (FIG. 17).

The edge and basal surfaces are defined by:

$$EA = \pi BT$$

$$BA = \pi B^2/2$$

hence fraction $f_e$ $$f_e = [Y+1]/[(Y+1)+(B/T)(1-Y^{-2n})(Y-1)] \quad (13)$$

1) When $n \to \infty$, $Y^{-2n} \to 0$ $$f_e = [Y+1]/[(Y+1)+(B/T)(Y-1)] \quad (14)$$

In these two models, it is possible to see that the trend in the basal and edge planes of the prismatic shape toward the spherical shape causes a noticeable decrease of the surface area of the basal planes. This increases the edge surface fraction in comparison to the total surface area of the particle. From the electrochemical point of view, passivation will be reduced with the reduction of the basal surface and on the other hand, intercalation will be more accessible over a large edge surface. For a given value of parameter (Y), where $Y \geq 1$, it is possible to compare the fraction of the edge surface $f_e$ obtained in equations 12 and 14. Tables 1.a-d present the results obtained for the edge fraction ($f_e$) calculated for the two approximations.

TABLE 1.A

Y = 1.001

| Particle size (μ) | B(μ) basal length | T(μ) edge length | $f_e$ prismatic | $f_e$ cylindrical | Gap (%) ($f_e$p-$f_e$c) |
|---|---|---|---|---|---|
| 2 | 2 | 0.21 | 0.99763 | 0.99526 | 0.2363 |
| 12 | 12 | 0.49 | 0.99392 | 0.98791 | 0.60089 |
| 20 | 20 | 1.54 | 0.99677 | 0.99355 | 0.32139 |
| 30 | 30 | 2.03 | 0.99632 | 0.99267 | 0.36523 |
| 40 | 40 | 2.85 | 0.99651 | 0.99303 | 0.34706 |

TABLE 2.B

Y = 1.01

| Particle size (μ) | B(μ) basal length | T(μ) edge length | $f_e$ prismatic | $f_e$ cylindrical | Gap (%) ($f_e$p-$f_e$c) |
|---|---|---|---|---|---|
| 2 | 2 | 0.21 | 0.97686 | 0.95476 | 2.2096 |
| 12 | 12 | 0.49 | 0.94258 | 0.89139 | 5.1185 |
| 20 | 20 | 1.54 | 0.96871 | 0.93931 | 2.9396 |
| 30 | 30 | 2.03 | 0.96454 | 0.93151 | 3.303 |
| 40 | 40 | 2.85 | 0.96626 | 0.93473 | 3.1533 |

TABLE 3.C

Y = 1.1

| Particle size (μ) | B(μ) basal length | T(μ) edge length | $f_e$ prismatic | $f_e$ cylindrical | Gap (%) ($f_e$p-$f_e$c) |
|---|---|---|---|---|---|
| 2 | 2 | 0.21 | 0.81516 | 0.68799 | 12.717 |
| 12 | 12 | 0.49 | 0.63168 | 0.46164 | 17.003 |
| 20 | 20 | 1.54 | 0.76382 | 0.61788 | 14.593 |
| 30 | 30 | 2.03 | 0.73972 | 0.58695 | 15.277 |
| 40 | 40 | 2.85 | 0.74953 | 0.5994 | 15.013 |

TABLE 4.D

Y = 1.5

| Particle size (μ) | B(μ) basal length | T(μ) edge length | $f_e$ prismatic | $f_e$ cylindrical | Gap (%) ($f_e$p-$f_e$c) |
|---|---|---|---|---|---|
| 2 | 2 | 0.21 | 0.5122 | 0.34426 | 16.793 |
| 12 | 12 | 0.49 | 0.28994 | 0.16955 | 12.039 |
| 20 | 20 | 1.54 | 0.43503 | 0.27798 | 15.705 |
| 30 | 30 | 2.03 | 0.40358 | 0.2528 | 15.078 |
| 40 | 40 | 2.85 | 0.41606 | 0.26267 | 15.339 |

The best approximation is normally obtained with a value of parameter Y closest to the unit. For Y=1.001, the value of $f_e$ in the approximations converges toward one, independently of the size of the particles. This means that the surface of basal planes I tends toward zero, which is the ideal case (Table 1a).

The gap between the two approximations increases with Y, as well as the effect of the particle size. When Y=1.01, there is a 3% gap between the two approximations and less than 2% between the size of the particles. While at Y=1.5, the gap is around 16%, while that between the particles remains between 2-3%.

This variation in factor $f_e$ depends on the way the shape of the elementary particles is considered, as well as the step between them (Y), which will form the final spherical particle. The divergence of $f_e$ from the unit gives the fraction of basal planes. In fact, the spherical form of the natural graphite particles is more advantageous and makes it possible to have a more rapid intercalation rate and less irreversible capacity (less basal surface).

2) When the term $(1-Y^{-2n})$ is considered in equations (11) and (13); if Y=1.1, the two equations rapidly converge (FIG. 3) after n iterations (n<50). As shown in FIG. 7, the results obtained show that:

the particles with small size are the easiest to make spherical (fe(2 ìm)>fe(40 ìm))

a prismatic approximation gives higher values for $f_e$.

The following examples, which are given purely by way of illustration, should not be interpreted as constituting any limitation of the present invention.

Example 1

Preparation of Potatolike Shaped Modified Graphite Particles from Natural Graphite Using Attrition Natural graphite is used that has an initial particle size of 375 μm, a purity rate 98% and in the shape of flakes. The specific surface area of this graphite is about 1 m²/g. The natural graphite powder is ground using an "attrition" process in order to transform these particles into spherical particles.

The $d_{002}$ has not changed after a change to spherical shape and has a value of 3.36 angstroms. Analysis using scanning electron microscopy (SEM) has shown, in micrograph 1a (FIG. 8) compared to micrograph 1b (FIG. 9) before attrition, the change in the shape of the particles while the size is essentially maintained at the same scale.

The fluorinated polyvinylidene PVDF bonding agent is solubilized in NMP N-methylpyrrolidone. An 80:20 mixture of the solvents acetone/toluene is added to the PVDF-NMP paste to form the coating composition. The natural graphite powder transformed into spheres is dispersed in the coating composition in a weight ratio of 90:10. This mixture is applied on a copper collector using the doctor blade method. The electrode is dried using an infrared lamp. The electrode is mounted in a 2035 button-type battery. A Celgard™ 2300 separator soaked with electrolyte 1M LiPF$_6$+EC/DMC: 50:50 (ethylene carbonate+dimethyl carbonate) is used.

Electrochemical tests were carried out at ambient temperature. The charge curves were obtained between O and 2.5 volts in C/24 for two button cells, P1 and P2 (FIG. 4), FIG. 10. The reversible capacity is 370 mAh/g. This result is comparable to that obtained with electrodes prepared using standard natural graphite in flake form, as well as artificial graphite in spherical form (MCMB28-25).

Example 2

Preparation of Potatolike Shaped Modified Graphite Particles from Natural Graphite Using Jet Milling Natural graphite is used comprising particles with initial size of 375 µm, purity rate 98% and in the shape of flakes. The specific surface area of this graphite is around 1 m$^2$/g. In a first step, the particles are reduced to 20 µm by jet milling. In a second step, the particles are cut to 10 µm in spherical shape by attrition.

Example 3

Preparation of Potatolike Shaped Modified Graphite Particles Using Jet Milling in the Presence of NH$_4$F 20 kg of Brazilian graphite with an average particle size (d$_{50}$) of 350 µm and a purity of 98.5% are mixed in a reactor with 10% by weight of NH$_4$F.

To homogenize the mixture, the jar mill method was used with ceramic balls having a diameter of 50 mm, for 24 hours. This mixture is ground by jet milling, the air pressure in the jet mill fluctuating between 100 and 125 psi during processing.

At the end of the processing, the average size of the particles is reduced to between 10 and 20 µm and the particles obtained have the shape of a potato.

FIG. 12, which is a scanning electron microscope micrograph, clearly shows the potatolike shape with a 12 µm particle.

FIG. 13, which is a scanning electron microscope micrograph, clearly shows that the basal function (fb) decreases and the edge function (fe) increases, thus the graphite planes at the basal level join the graphite planes at the level of the edge in the form of a saw tooth (verification of mathematical model 1).

Example 4

Preparation of Potatolike Shaped Modified Graphite Particles by Attrition and in the Presence of NaCl 20 kg of Brazilian graphite with an average particle size (d$_{50}$) of 350 µm and a purity of 98.5% is mixed in a reactor with 10% by weight of NaCl.

Homogenization of the mixture is carried out using the jar mill method with ceramic balls having a diameter of 50 mm, for 24 hours.

This mixture is ground by jet milling. The dwell time of the mixture in the chamber is 45 minutes.

During processing, air pressure in the jet mill fluctuates between 100 and 125 psi. In the course of processing, the size of the particles is reduced to between 10 and 20 µm and the shape of the particles obtained is potatolike.

The scanning electron microscope micrograph (MEB), FIG. 14, clearly shows the potatolike shape obtained with a 12 µm particle.

The scanning electron microscope micrograph (FIG. 15) clearly shows that the basal function (fb) decreases and that the edge function (fe) increases, a result of the rounding of the particle (verification of mathematical model 1).

Example 5

Preparation of Particles Based on Graphite Having a Core Coated with a Layer of Carbonated Cellulose Carbonate In a 200 ml container, a mixture is prepared of 2 g of Brazilian graphite with an average particle size (d$_{50}$) of 20 µm and prismatic shape, and 10% cellulose acetate.

The mixture is dissolved in acetone and homogenized using the ball mill method. The mixture is processed at 400° C. for 3 hours in a nitrogen atmosphere.

The particles obtained are potatolike shaped.

One of the advantages of this treatment is that the carbonated layer obtained on the surface plays the role of purifier since it covers all the impurities existing at the surface.

Example 6

Preparation of Graphite-Based Particles Having a Core Coated with a Layer of Carbonated PE-PEO-Glycol In a 200 ml reactor, a mixture of 2 g of Brazilian graphite with an average particle size (d$_{50}$) of 20 µm and prismatic shape, and 10% of the PE-PEO-glycol compound is prepared.

The mixture is dissolved in acetone, then it is homogenized by ball milling. The mixture is processed at 400° C. for 3 hours in a nitrogen atmosphere.

The particles obtained are potatolike shaped.

One of the advantages of this treatment is that the carbonated layer obtained on the surface plays the role of a purifier since it covers all the impurities present at the surface.

Example 7

Preparation of Graphite-Based Particles Having a Core Coated with a Layer of Silver A Brazilian graphite with an average particle size (d$_{50}$) of 20 µm and prismatic shape, with a purity of 98.5%, is covered on its surface with a 10% by weight silver deposit.

The deposit is obtained by evaporation, using an Edwards Coating System Model E306A evaporator.

The reversible capacity is 387 mAh/g, 15 mA/g more than the theoretical capacity of natural graphite.

A low specific surface area is associated with a lower passivation film contribution. Within the scope of the present invention, it has thus been established that this passivation layer forms on the basal part (organic species): ICL$_{basal}$ and on the edge part (inorganic species): ICL$_{edge}$. In summary, ICL$_{basal}$ is 40 times higher than ICL$_{edge}$. This shows that the decrease in the basal function is very important in order to reduce the irreversible capacity and the exhaust of gases. This is associated with the safety of the battery.

The invention claimed is:
1. A process for preparing modified graphite-based particles comprising:
coating a surface of prismatic-shaped graphite-based particles with a metallic deposit or with a metallic and carbonic deposit while keeping a basal function (fb) and an edge function (fe) of the prismatic-shaped graphite-based particles constant,
wherein the coating of the surface of the prismatic-shaped graphite-based particles results in a sphericity of 80% or more.

2. The method of claim 1, wherein the modified graphite-based particles comprise at least one characteristic selected from the group consisting of a tap density between 0.3 and 1.5 g/cc; a granulometric dispersion such that a D90/D10 ratio varies between 2 and 5; and a size between 1 and 50 µm.

3. The method of claim 1, wherein the coating of the surface of the prismatic-shaped graphite-based particles with the metallic deposit or with the metallic and carbonic deposit comprises disposing the graphite-based particles in a solvent with a metallic and/or carbonic source followed by homogenizing by milling.

4. The method of claim 3, wherein the milling comprises ball milling.

5. The method of claim 1, wherein the coating of the surface of the prismatic-shaped graphite-based particles with the metallic deposit or with the metallic and carbonic deposit comprises evaporating a metallic and/or carbonic source onto the surface of the prismatic-shaped graphite-based particles.

6. A process for preparing modified graphite-based particles comprising:
coating a surface of natural graphite-based particles with a metallic deposit or with a metallic and carbonic deposit while keeping a basal function (fb) and an edge function (fe) of the graphite-based particles constant,
wherein the coating of the surface of the natural graphite-based particles results in a sphericity of 80% or more.

7. The method of claim 6, wherein the modified graphite-based particles comprise at least one characteristic selected from the group consisting of a tap density between 0.3 and 1.5 g/cc; a granulometric dispersion such that a D90/D10 ratio varies between 2 and 5; and a size between 1 and 50 µm.

8. The method of claim 6, wherein the coating of the surface of the natural graphite-based particles with the metallic deposit or with the metallic and carbonic deposit comprises disposing the graphite-based particles in a solvent with a metallic and/or carbonic source followed by homogenizing by milling.

9. The method of claim 8, wherein the milling comprises ball milling.

10. The method of claim 6, wherein the coating of the surface of the natural graphite-based particles with the metallic deposit or with the metallic and carbonic deposit comprises evaporating a metallic and/or carbonic source onto the surface of the natural graphite-based particles.

11. A process for preparing modified graphite-based particles comprising:
coating natural graphite-based particles with a metallic deposit or with a metallic and carbonic deposit, wherein the modified graphite-based particles, prior to coating, have a first basal function (fb) and a first edge function (fe), wherein the modified graphite-based particles have a second basal function (fb) and a second edge function (fe),
wherein the second edge function is greater than the first edge function and the second basal function is smaller than the first basal function.

12. The method of claim 11, wherein the modified graphite-based particles comprise at least one characteristic selected from the group consisting of a tap density between 0.3 and 1.5 g/cc; a granulometric dispersion such that a D90/D10 ratio varies between 2 and 5; and a size between 1 and 50 µm.

13. The method of claim 11, wherein the coating of the surface of the natural graphite-based particles with the metallic deposit or with the metallic and carbonic deposit comprises disposing the graphite-based particles in a solvent with a metallic and/or carbonic source followed by homogenizing by milling.

14. The method of claim 13, wherein the milling comprises ball milling.

15. The method of claim 11, wherein the coating of the surface of the natural graphite-based particles with the metallic deposit or with the metallic and carbonic deposit comprises evaporating a metallic and/or carbonic source onto the surface of the natural graphite-based particles.

16. A process for preparing modified graphite-based particles comprising:
coating prismatic-shaped graphite-based particles with a metallic deposit or with a metallic and carbonic deposit, wherein the prismatic-shaped graphite-based particles, prior to coating, have a first basal function (fb) and a first edge function (fe), wherein the modified graphite-based particles have a second basal function (fb) and a second edge function (fe),
wherein the second edge function is greater than the first edge function and the second basal function is smaller than the first basal function.

17. The method of claim 16, wherein the modified graphite-based particles comprise at least one characteristic selected from the group consisting of a tap density between 0.3 and 1.5 g/cc; a granulometric dispersion such that a D90/D10 ratio varies between 2 and 5; and a size between 1 and 50 µm.

18. The method of claim 16, wherein the coating of the surface of the prismatic-shaped graphite-based particles with the metallic deposit or with the metallic and carbonic deposit comprises disposing the graphite-based particles in a solvent with a metallic and/or carbonic source followed by homogenizing by milling.

19. The method of claim 18, wherein the milling comprises ball milling.

20. The method of claim 16, wherein the coating of the surface of the prismatic-shaped graphite-based particles with the metallic deposit or with the metallic and carbonic deposit comprises evaporating a metallic and/or carbonic source onto the surface of the prismatic-shaped graphite-based particles.

* * * * *